(12) United States Patent
Markosyan

(10) Patent No.: US 8,993,028 B2
(45) Date of Patent: *Mar. 31, 2015

(54) PROCESS FOR THE PURIFICATION OF HIGH-PURITY RUBUSOSIDE

(75) Inventor: Avetik Markosyan, Kuala Lumpur (MY)

(73) Assignee: PureCircle Sdn Bhd, Negeri Sembilan (MY)

( * ) Notice: Subject to any disclaimer, the term of this patent is extended or adjusted under 35 U.S.C. 154(b) by 342 days.

This patent is subject to a terminal disclaimer.

(21) Appl. No.: 13/553,820

(22) Filed: Jul. 20, 2012

(65) Prior Publication Data

US 2013/0040033 A1    Feb. 14, 2013

Related U.S. Application Data

(60) Provisional application No. 61/522,237, filed on Aug. 10, 2011.

(51) Int. Cl.
*A23L 1/236* (2006.01)
*C07H 15/24* (2006.01)
*C07H 1/08* (2006.01)

(52) U.S. Cl.
CPC .............. *C07H 15/24* (2013.01); *A23L 1/2366* (2013.01); *C07H 1/08* (2013.01)

USPC ............ 426/548; 426/425; 426/429; 426/431

(58) Field of Classification Search
USPC .................................. 426/425, 429, 431, 548
See application file for complete search history.

(56) References Cited

U.S. PATENT DOCUMENTS 8,299,224 B2 * 10/2012 Abelyan et al. ............... 536/18.1
8,501,261 B2 * 8/2013 Markosyan .................... 426/548
2011/0033525 A1    2/2011 Liu

FOREIGN PATENT DOCUMENTS

WO    WO2011090709 A1    7/2011

* cited by examiner

*Primary Examiner* — Leslie Wong
(74) *Attorney, Agent, or Firm* — Pyprus Pte Ltd

(57) ABSTRACT

The invention provides a process of purifying Rubusoside from the *Rubus suavissimus* S. Lee plant extract. The process is useful for producing high purity Rubusoside with purity greater than 95% (dry basis). High purity rubusoside is useful as in combination with other caloric and non-caloric sweeteners as well as non-caloric sweetener in various food and beverage compositions. The high purity rubusoside is useful as non-caloric sweetener in edible and chewable compositions such as any beverages, confectioneries, bakeries, cookies, chewing gums, and alike.

8 Claims, 1 Drawing Sheet

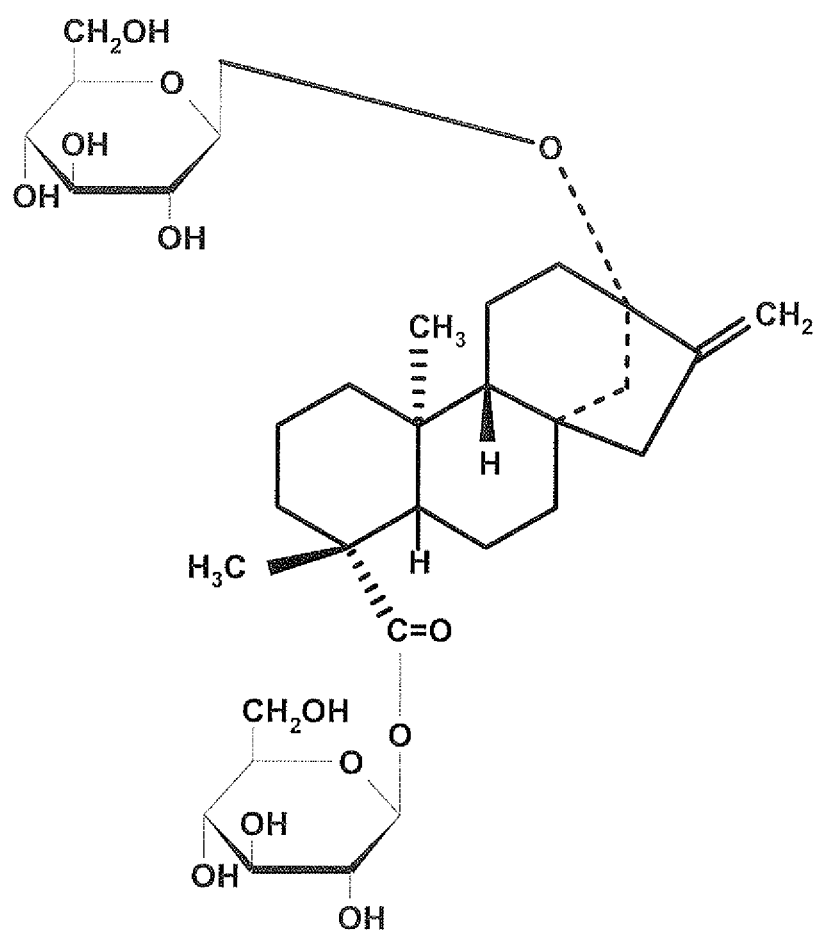

PROCESS FOR THE PURIFICATION OF HIGH-PURITY RUBUSOSIDE

RELATED APPLICATION

This application claims the benefit under 35 U.S.C. 119(e) of U.S. provisional application Ser. No. 61/522,237 entitled "High-Purity Rubusoside And Process For Purification Of The Same", filed Aug. 10, 2011, which is herein incorporated by reference.

FIELD OF THE INVENTION

The invention relates to a process for isolation and purification of individual sweet glycosides of *Rubus suavissimus* S. Lee, and more particularly to a process isolation and purification of Rubusoside from *Rubus suavissimus* S. Lee plant extract.

BACKGROUND OF THE INVENTION

Nowadays high intensity sweeteners are used worldwide. They can be of both synthetic and natural origin.

Non-limiting examples of synthetic sweeteners include sucralose, potassium acesulfame, aspartame, alitame, saccharin, neohesperidin dihydrochalcone synthetic derivatives, cyclamate, neotame, dulcin, suosan, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

Non-limiting examples of natural high intensity sweeteners include Stevioside, Rebaudioside A, Rebaudioside B, Rebaudioside C, Rebaudioside E, Rebaudioside F, Steviolbioside, Dulcoside A, Rubusoside, mogrosides, brazzein, neohesperidin dihydrochalcone (NHDC), glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobtain, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, siamenoside and others.

The standard sweetening power associated with each high intensity sweetener is given in TABLE 1. However, when they are used in blends, the sweetening power can change significantly.

TABLE 1

| Sweetener | Sweetness power |
|---|---|
| Saccharose | 1 |
| Acesulfame-K | 200 |
| Alitame | 2000 |
| Aspartame | 200 |
| Cyclamate | 30 |
| Glycyrrhizin | 50 |
| NHDC | 1000 |
| Saccharine | 300 |
| Stevioside | 200 |
| Rebaudioside A | 450 |

TABLE 1-continued

| Sweetener | Sweetness power |
|---|---|
| Thaumatin | 3000 |
| Sucralose | 600 |

*Stevia rebaudiana* Bertoni is a perennial shrub of the Asteraceae (Compositae) family native to certain regions of South America. The leaves of the plant contain from 10 to 20% of diterpene glycosides, which are around 150 to 450 times sweeter than sugar. The leaves have been traditionally used for hundreds of years in Paraguay and Brazil to sweeten local teas and medicines.

At present there are more than 230 *Stevia* species with significant sweetening properties. The plant has been successfully grown under a wide range of conditions from its native subtropics to the cold northern latitudes.

Steviol glycosides have zero calories and can be used wherever sugar is used. They are ideal for diabetic and low calorie diets. In addition, the sweet steviol glycosides possess functional and sensory properties superior to those of many high potency sweeteners.

The extract of *Stevia rebaudiana* plant contains a mixture of different sweet diterpene glycosides, which have a single base—steviol and differ by the presence of carbohydrate residues at positions C13 and C19. These glycosides accumulate in *Stevia* leaves and compose approximately 10%-20% of the total dry weight. Typically, on a dry weight basis, the four major glycosides found in the leaves of Stevia are Dulcoside A (0.3%), Rebaudioside C (0.6-1.0%), Rebaudioside A (3.8%) and Stevioside (9.1%). Other glycosides identified in *Stevia* extract include Rebaudioside B, D, E, and F, Steviolbioside and Rubusoside. Among steviol glycosides only Stevioside and Rebaudioside A are available in commercial scale.

The physical and sensory properties are well studied only for Stevioside and Rebaudioside A. The sweetness potency of Stevioside is around 210 times higher than sucrose, Rebaudioside A in between 200 and 400 times.

On the other hand commercial preparations of steviol glycosides such as *Stevia* Extract, Rebaudioside A possess certain drawbacks substantially limiting their usage in mainstream products.

It has to be noted that high intensity sweeteners' taste profile is highly dependant on the concentration and usually the higher the concentration the higher the sensation of undesirable taste components such as bitterness, licorice, lingering aftertaste. This phenomenon limits the usage of steviol glycosides further to 4-5% sucrose equivalents in order to achieve pleasant taste of a food or beverage sweetened with *stevia* sweeteners.

Therefore in many cases various sweeteners are used in blends to benefit from the effect of synergism, which allows the usage of sweeteners at lower concentrations where undesirable taste profile attributes are less prominent. It has to be noted that synergistic effect can be achieved both between different high intensity sweeteners as well as between high intensity and bulk sweeteners such as sucrose etc.

Rubusoside (CAS No: 64849-39-4), is one of the sweet sweet glycosides found in *Stevia rebaudiana*. Its concentration in dried leaves of Stevia is usually <0.2%. The chemical structure of Rubusoside is shown in FIG. 1. However, unlike other steviol glycosides present in *Stevia*, rubusoside is also found in leaves of *Rubus suavissimus* S. Lee (Chinese sweet leaf). Rubusoside is the main steviol glycoside found in the leaves of *Rubus suavissimus*.

Recent studies show that Rubusoside possess certain valuable properties. Particularly WIPO Patent Application WO/2011/090709 describes sweetness-enhancing properties of Rubusoside. U.S. patent application Ser. No. 12/937,055 describe Rubusoside usage as a natural solubilizing agent for a number of compounds.

These properties multiply the significance of Rubusoside and attract great interest for processes of preparation of highly purified forms of Rubusoside.

There are few processes described for Rubusoside preparation.

WIPO Patent Application WO/2011/090709 describes a process for preparing high purity rubusoside wherein the commercial crude Rubusoside extract (63.7% purity) was dissolved in aqueous methanol and subjected to chromatographic purification on a column packed with reverse-phase stationary phase. The fractions with high Rubusoside content were combined, dried and refluxed with methanol, to prepare Rubusoside having 94.6% purity. It has to be noted that employing chromatographic separation techniques in large scale production is not feasible and is suitable generally for Lab or pilot scale processes.

U.S. patent application Ser. No. 12/937,055 describes a process for Rubusoside preparation wherein *Rubus suavissimus* dried leaves were extracted with water and the water extract was dried to yield a crude extract containing 5-15% rubusoside (w/w). The dried crude extract was dissolved in water and subjected to column chromatography with macroporous adsorbent. As a result Rubusoside was adsorbed on macroporous resin and subsequently eluted with ethanol to obtain a purified extract containing ca. 60% rubusoside. Subsequently, the purified extract was subjected to chromatography on a column packed with silicagel and the fractions rich in Rubusoside were dried to yield Rubusoside with ca. 80% purity. The said material was further re-crystallized from Methanol to yield rubusoside with >99% purity. As discussed above, processes utilizing chromatographic techniques are suitable for Lab or pilot scale production only.

In both above-mentioned inventions there is a necessity to utilize chromatographic separation (reverse phase or silicagel) to purify Rubusoside to approx. 80% purity, which subsequently is purified by refluxing or recrystallization with organic solvent. This preliminary purification is necessary because the crude *Rubus suavissimus* extracts have very high solubility in water and organic solvents and therefore cannot be crystallized directly.

Thus it can be concluded, there is a need for a simple, efficient, and economical process for production of high purity Rubusoside.

SUMMARY OF THE INVENTION

The invention relates to a process for isolation and purification of steviol glycosides from *Rubus suavissimus* S. Lee plant, and more particularly to a process for isolation and purification of Rubusoside.

The primary objective of the invention is to develop an efficient process of isolating and purifying Rubusoside from *Rubus suavissimus* extract.

One aspect of the present invention provides a process for purifying Rubusoside from *Rubus suavissimus* extract. In one embodiment, the process comprises steps of:
 a. providing an extract of *Rubus suavissimus* S. Lee leaves;
 b. dissolving the extract in a first aqueous alcoholic solution to obtain a first mixture;
 c. inducing crystallization in the first mixture by temperature gradient treatment;
 d. filtering the first mixture from (c) to obtain a first precipitate and a first filtrate;
 e. dissolving the first precipitate in a second aqueous alcoholic solution to obtain a second mixture;
 f. adding activated carbon to the second mixture and filtering it to obtain decolorized second mixture;
 g. inducing crystallization in the decolorized second mixture by temperature gradient treatment;
 h. filtering the decolorized second mixture from (g) to obtain a second precipitate and a second filtrate;
 i. suspending the second precipitate in a third aqueous alcoholic solution to obtain a third mixture;
 j. filtering the third mixture to obtain a third precipitate and a third filtrate; and
 k. drying the third precipitate to yield purified Rubusoside.

In another embodiment of the process, the first aqueous alcoholic solution in step (b) is a methanol-water solution, with 75-99% methanol.

In another embodiment of the process, the second aqueous alcoholic solution in step (e) is a methanol-water solution with 70-90% methanol.

In another embodiment of the process, the third aqueous alcoholic solution in step (i) is a methanol-water solution with 90-99% methanol.

In another embodiment of the process, in steps (c) and (g) the temperature gradient treatment inducing crystallization comprises increasing the mixture temperature to 65-70° C. then gradually cooling it to 10° C. at a rate of 10° C. per hour with continuous mild agitation.

In another embodiment of the process, the aqueous alcoholic solutions comprise one or more organic solvents selected from the group consisting of methanol, ethanol, 1-propanol, and isopropanol.

In another embodiment of the process, the purified Rubusoside has purity greater than 95% on a dry basis.

In another embodiment of the process, the purified Rubusoside has purity greater than 98% on a dry basis.

Another aspect of the present invention provides a product comprising high purity Rubusoside, wherein the product is selected from the group consisting of food, beverage, pharmaceutical composition, tobacco, nutraceutical, oral hygienic composition, or cosmetic.

Another aspect of the present invention provides a sweetener composition comprising high purity Rubusoside.

In another embodiment, the sweetener composition further comprises Rebaudioside A, enzymatically modified stevia, Rebaudioside D, a mixture of steviol glycosides with more than 95% (on dry basis) total steviol glycosides content, high intensity sweetener and natural flavor compound, caloric sweetener, or sucrose.

In another embodiment, the sweetener composition further comprises one natural high intensity sweetener selected from the group consisting of: steviol glycosides including a purified sweet steviol glycoside mixture, stevioside, rebaudioside A, rebaudioside B, rebaudioside C, rebaudioside D, rebaudioside E, rebaudioside F, dulcoside A, dulcoside B, stevia, alpha-glucosyl stevia, fructosyl stevia, galactosyl stevia, beta-glucosyl stevia; siamenoside; mogroside IV; mogroside V; Luo Han Guo sweetener; monatin and its salts (monatin SS, RR, RS, SR); glycyrrhizic acid and its salts; curculin; thaumatin; monellin; mabinlin; brazzein; hernandulcin; phyllodulcin; glycyphyllin; phloridzin; trilobtain; baiyunoside; osladin; polypodoside A; pterocaryoside A; pterocaryoside B; mukurozioside; phlomisoside I; periandrin I; abrusoside A; cyclocarioside I; and combinations thereof.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

BRIEF DESCRIPTION OF THE DRAWINGS

Preferred embodiments according to the present invention will now be described with reference to the Figures, in which like reference numerals denote like elements.

FIG. 1 is the chemical structure of Rubusoside.

DETAILED DESCRIPTION OF THE INVENTION

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention provides a process for isolation and purification of rubusoside.

In one embodiment of present invention, the process of the isolation and purification begins with providing *Rubus suavissimus* extract, containing 30-60%, preferably 40-60% (on dry basis) rubusoside. The extract is admixed with a first aqueous alcoholic solution containing 70-100%, more preferably 75-99% alcohol to obtain a first mixture. The ratio (wt/vol) of extract (kg) to aqueous alcohol is 1:1 to 1:5, more preferably 1:1 to 1:4. The alcohol is selected from the group comprising ethanol, methanol, 1-propanol, 2-propanol or combinations thereof, more preferably ethanol and methanol.

In another embodiment the first mixture is incubated at a temperature 10-100° C. more preferably 30-80° C. for 0.5-30 min more preferably for 1-10 min.

In another embodiment the first mixture is then cooled to 0-40° C. preferably 10-20° C. at a rate of 8-11° C. per hour, and incubated at final temperature for 1-72 hours, preferably 1-24 hours to facilitate the crystallization of Rubusoside.

In another embodiment the crystallized Rubusoside is separated from the first mixture to become a first precipitate, and the remaining solution becomes a first filtrate.

In another embodiment the first precipitate has 75-95%, preferably 80-90% (on dry basis) Rubusoside content.

In another embodiment the first precipitate is admixed with a second aqueous alcoholic solution containing 60-100%, more preferably 70-90% alcohol to obtain a second mixture. The ratio (wt/vol) of the first precipitate (kg) to aqueous alcohol (liter) is 1:1 to 1:5, more preferably 1:2 to 1:4. The alcohol is selected from the group comprising ethanol, methanol, 1-propanol, 2-propanol or combinations thereof, more preferably ethanol and methanol.

In another embodiment the second mixture is heated till full dissolution of first precipitate and 1-5%, preferably 1-2% of activated carbon is added and the mixture is incubated for 20 min at 60-70° C. Subsequently the activated carbon is removed by means of press filter to obtain the decolorized second mixture.

In another embodiment the decolorized second mixture is incubated at a temperature 10-100° C. more preferably 30-80° C. for 0.5-30 min more preferably for 1-10 min.

In another embodiment the decolorized second mixture is then cooled to 0-40° C. preferably 10-20° C. at a rate of 8-11° C. per hour, and incubated at final temperature for 1-72 hours, preferably 1-24 hours to facilitate the crystallization of Rubusoside.

In another embodiment the crystallized Rubusoside is separated from the decolorized second mixture to become a second precipitate, and the remaining solution becomes a second filtrate.

In another embodiment the second precipitate has 90-100%, preferably 95-100% (on dry basis) Rubusoside content.

In another embodiment the second precipitate is further suspended in a third aqueous alcoholic solution containing 70-100%, more preferably 90-99% alcohol to obtain a third mixture. The ratio (wt/vol) of the second precipitate (kg) to aqueous alcohol (liter) is 1:1 to 1:5, more preferably 1:1 to 1:2. The alcohol is selected from the group comprising ethanol, methanol, 1-propanol, 2-propanol or combinations thereof, more preferably ethanol and methanol.

In another embodiment the third mixture is then incubated at 0-40° C. preferably 10-30° C. for 1-144 hours, preferably 24-72 hours.

In another embodiment the third mixture is separated into a third precipitate and a third filtrate, where the third precipitate has >98% rubusoside content (on dry basis).

In another embodiment the third precipitate is dried by any means known to art to provide dry crystalline powder.

The HPLC analysis of steviol glycosides was carried out as described in FAO JECFA Monographs 10 (2010), using an Agilent Technologies (USA) "1200 series" chromatograph, equipped with Luna C18(2) 100A (Phenomenex, USA) column (4.6×250 mm, 5 μm), using 32:68 (v/v) mixture of acetonitrile and 10 mmol/L sodium phosphate buffer (pH 2.6) as mobile phase, and UV detector at 210 nm.

The obtained highly purified rubusoside preparations can be used as sweetness enhancer, flavor enhancer and sweetener in various food and beverage products. Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, tabletop sweeteners, fruits and vegetables.

Additionally the highly purified rubusoside preparations can be used in drug or pharmaceutical preparations and cosmetics, including but not limited to toothpaste, mouthwash, cough syrup, chewable tablets, lozenges, vitamin preparations, and the like.

The highly purified rubusoside preparations can be used "as-is" or in combination with other sweeteners, flavors and food ingredients.

Non-limiting examples of sweeteners include steviol glycosides, stevioside, rebaudioside A, rebaudioside B, rebaudioside C, rebaudioside D, rebaudioside E, rebaudioside F, dulcoside A, steviolbioside, as well as other steviol glycosides found in *Stevia rebaudiana* Bertoni plant and mixtures thereof, *stevia* extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols.

Non-limiting examples of flavors include lemon, orange, fruity, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners, gelling agents.

The following examples illustrate preferred embodiments of the invention.

EXAMPLE 1

Purification of Rubusoside 2 kg of *Rubus suavissimus* extract produced by "Guangzhou Wei Guan Trade Co., Ltd" (China), and containing 40.6% (on dry basis) rubusoside was dissolved in 6 liters of 98% methanol and the mixture was heated to 60° C. and maintained for 10 min. Then the mixture was cooled to 10° C. at a rate of 10° C. per hour. During the cooling the mixture was subjected to continuous moderate agitation. Starting from about 15° C. fine crystals were formed. The amount of crystals subsequently increased. The mixture was incubated at 10° C. during 24 hrs. The crystals were separated by filtration and washed on the filter by pure methanol preliminarily chilled to 4° C. The obtained crystals were dried under vacuum at 80° C. to yield about 850 g crystals with 82.3% rubusoside content (dry basis).

EXAMPLE 2

Purification of Rubusoside 1 kg of Rubusoside prepared as per EXAMPLE 1, with 82.0% Rubusoside content, was dissolved in 4 liters of 85% methanol at 70° C. Then 50 g of activated carbon was added to mixture and maintained at 70° C. for 20 min. The carbon was removed through Lab press filter and the obtained decolorized filtrate was heated to 70° C. and maintained for 10 min. Then the mixture was cooled to 10° C. at a rate of 10° C. per hour. During the cooling the mixture was subjected to continuous moderate agitation. Starting from about 15° C. fine crystals were formed. The amount of crystals subsequently increased. The mixture was incubated at 10° C. during 24 hrs. The crystals were separated by filtration and washed on the filter by pure methanol preliminarily chilled to 4° C. The obtained crystals were dried under vacuum at 80° C. to yield about 790 g crystals with 96.3% rubusoside content (dry basis).

EXAMPLE 3

Refining of Rubusoside 500 g of Rubusoside prepared as per EXAMPLE 2 was suspended in 1000 mL of 92% methanol at room temperature. The mixture was heated and maintained at 30° C. during 48 hours. The crystals were separated by filtration and washed on the filter by pure methanol. The obtained crystals were dried under vacuum at 80° C. to yield about 450 g crystals with 98.5% rubusoside content (dry basis).

I claim:

1. A process for purifying Rubusoside from *Rubus suavissimus* extract comprising the steps of:
   a. providing an extract of *Rubus suavissimus* S. Lee leaves;
   b. dissolving the extract in a first aqueous alcoholic solution to obtain a first mixture;
   c. inducing crystallization in the first mixture by temperature gradient treatment;
   d. filtering the first mixture from (c) to obtain a first precipitate and a first filtrate;
   e. dissolving the first precipitate in a second aqueous alcoholic solution to obtain a second mixture;
   f. adding activated carbon to second mixture and filtering it to obtain a decolorized second mixture;
   g. inducing crystallization in the decolorized second mixture by temperature gradient treatment;
   h. filtering the decolorized second mixture from (g) to obtain a second precipitate and a second filtrate;
   i. suspending the second precipitate in a third aqueous alcoholic solution to obtain a third mixture;
   j. filtering the third mixture to obtain a third precipitate and a third filtrate; and
   k. drying the third precipitate to yield purified Rubusoside.

2. The process of claim 1 wherein the first aqueous alcoholic solution in step (b) is a methanol-water solution, with 75-99% methanol.

3. The process of claim 1 wherein the second aqueous alcoholic solution in step (e) is a methanol-water solution with 70-90% methanol.

4. The process of claim 1 wherein the third aqueous alcoholic solution in step (i) is a methanol-water solution with 90-99% methanol.

5. The process of claim 1 wherein in steps (c) and (g) the temperature gradient treatment inducing crystallization comprises increasing the mixture temperature to 65-70° C. then gradually cooling it to 10° C. at a rate of 10° C. per hour with continuous mild agitation.

6. The process of claim 1 wherein the aqueous alcoholic solutions comprises one or more organic solvents selected from the group consisting of methanol, ethanol, 1-propanol, and isopropanol.

7. The process of claim 1, wherein the purified Rubusoside has a purity greater than 95% on a dry basis.

8. The process of claim 1, wherein the purified Rubusoside has a purity greater than 98% on a dry basis.

\* \* \* \* \*